(12) United States Patent
Kantonen et al.

(10) Patent No.: US 9,182,362 B2
(45) Date of Patent: Nov. 10, 2015

(54) APPARATUS FOR PROTECTING A RADIATION WINDOW

(71) Applicant: Bruker AXS Handheld, Inc., Kennewick, WA (US)

(72) Inventors: Esko Juhani Kantonen, Helsinki (FI); Erkki Tapani Puusaari, Espoo (FI); Heikki Johannes Sipila, Espoo (FI)

(73) Assignee: BRUKER AXS HANDHELD, INC., Kennewick, WA (US)

( * ) Notice: Subject to any disclaimer, the term of this patent is extended or adjusted under 35 U.S.C. 154(b) by 238 days.

(21) Appl. No.: 13/866,662

(22) Filed: Apr. 19, 2013

(65) Prior Publication Data

US 2013/0279654 A1    Oct. 24, 2013

Related U.S. Application Data

(60) Provisional application No. 61/636,334, filed on Apr. 20, 2012.

(51) Int. Cl.
*G01N 23/223*    (2006.01)
*H01J 35/18*    (2006.01)

(52) U.S. Cl.
CPC .............. *G01N 23/223* (2013.01); *H01J 35/18* (2013.01); *G01N 2223/076* (2013.01)

(58) Field of Classification Search
CPC ........... G01N 23/223; H01J 5/18; H01J 35/18
USPC .............................................. 378/44–50, 161
See application file for complete search history.

(56) References Cited

U.S. PATENT DOCUMENTS

| | | | |
|---|---|---|---|
| 2,965,759 A † | 12/1960 | Eberline | |
| 4,617,465 A | 10/1986 | Yoshida | |
| 4,933,557 A | 6/1990 | Perkins et al. | |
| 5,017,245 A | 5/1991 | Suzuki et al. | |
| 5,039,203 A | 8/1991 | Nishikawa | |
| 5,161,179 A | 11/1992 | Suzuki et al. | |
| 5,226,067 A * | 7/1993 | Allred et al. | 378/161 |
| 5,329,569 A | 7/1994 | Spielman | |
| 5,355,399 A | 10/1994 | Golovanivsky et al. | |

(Continued)

FOREIGN PATENT DOCUMENTS

WO    2011151505 A1    12/2011

OTHER PUBLICATIONS

International Search Report and Written Opinion, dated Jul. 9, 2013, for co-pending International Application No. PCT/US2013/037461 filed Apr. 19, 2013.

(Continued)

*Primary Examiner* — Allen C. Ho
(74) *Attorney, Agent, or Firm* — Armstrong Teasdale LLP

(57) ABSTRACT

A radiation detector assembly and a method for using the same are provided. The radiation detector assembly includes an aperture, a window covering the aperture, the window is configured to permit radiation to pass through, the window is configured to prevent the passage of fluids and particles through the aperture, and a protective device covers the window. The protective device includes a plurality of holes at least partially aligned with the aperture, is configured to permit at least some radiation to pass through the holes, is configured to prevent objects larger than the holes to contact the window and is configured to withstand external forces and prevent those forces from damaging the window.

19 Claims, 6 Drawing Sheets

(56) References Cited

U.S. PATENT DOCUMENTS

| | | | |
|---|---|---|---|
| 5,519,752 A | 5/1996 | Spielman | |
| 5,832,054 A * | 11/1998 | Kuwabara | 378/45 |
| 6,449,338 B1 | 9/2002 | Bacal Verney et al. | |
| 6,477,227 B1 * | 11/2002 | Kaiser et al. | 378/45 |
| 6,501,825 B2 * | 12/2002 | Kaiser et al. | 378/45 |
| 6,801,595 B2 * | 10/2004 | Grodzins et al. | 378/45 |
| 6,850,592 B2 * | 2/2005 | Schramm et al. | 378/45 |
| 7,020,238 B1 * | 3/2006 | Kantonen et al. | 378/44 |
| 7,035,379 B2 | 4/2006 | Turner et al. | |
| 7,065,174 B2 * | 6/2006 | Sipila et al. | 378/44 |
| 7,233,647 B2 | 6/2007 | Turner et al. | |
| 7,375,359 B1 * | 5/2008 | Grodzins | 378/45 |
| 7,409,037 B2 * | 8/2008 | Puusaari et al. | 378/44 |
| 7,430,274 B2 * | 9/2008 | Connors et al. | 378/44 |
| 7,443,951 B2 * | 10/2008 | Kenning et al. | 378/44 |
| 7,443,959 B2 * | 10/2008 | Kantonen et al. | 378/147 |
| 7,474,730 B2 * | 1/2009 | Puusaari et al. | 378/48 |
| 7,508,906 B2 * | 3/2009 | Puusaari et al. | 378/44 |
| 7,709,820 B2 | 5/2010 | Decker et al. | |
| 7,737,424 B2 | 6/2010 | Xu et al. | |
| 7,756,251 B2 | 7/2010 | Davis et al. | |
| 7,916,834 B2 | 3/2011 | Piorek et al. | |
| 8,155,268 B2 * | 4/2012 | Pesce et al. | 378/45 |
| 8,494,113 B2 * | 7/2013 | Grodzins | 378/45 |
| 8,498,381 B2 * | 7/2013 | Liddiard et al. | 378/161 |
| 8,787,523 B2 * | 7/2014 | Sackett | 378/44 |
| 8,835,857 B2 * | 9/2014 | Eggert | 378/44 |
| 8,929,515 B2 * | 1/2015 | Liddiard | 378/140 |
| 2003/0002627 A1 | 1/2003 | Espinosa et al. | |
| 2004/0251431 A1 | 12/2004 | Yamaguchi et al. | |
| 2008/0192889 A1 | 8/2008 | Rohde et al. | |
| 2008/0296479 A1 | 12/2008 | Anderson et al. | |
| 2010/0080351 A1 | 4/2010 | Hession-Kunz et al. | |
| 2011/0121179 A1 * | 5/2011 | Liddiard et al. | 250/336.1 |
| 2011/0311029 A1 | 12/2011 | Andersson | |
| 2013/0268210 A1 * | 10/2013 | Patterson | 378/45 |

OTHER PUBLICATIONS

Burgess, P.H., "Handbook on measurement methods and strategies at very low levels and activities", European Commission Nuclear Safety and the Environment, Report EUR 17624, Feb. 1998.

\* cited by examiner
† cited by third party

APPARATUS FOR PROTECTING A RADIATION WINDOW

CROSS REFERENCE TO RELATED APPLICATIONS

This application claims priority to and the benefit of the filing date of U.S. Provisional Application No. 61/636,334 filed on Apr. 20, 2012, which is hereby incorporated by reference in its entirety.

BACKGROUND OF THE INVENTION

The embodiments described herein relate generally to X-ray devices that include a window through which X-rays are transmitted, and more specifically, to protecting the window from external forces.

X-ray devices, for example, an X-ray source or an X-ray detector, may utilize a vacuum chamber with a window through which X-rays are transmitted. For example, a beryllium window may facilitate maintaining the vacuum within the vacuum chamber while also allowing X-rays to enter and/or leave the chamber. The transmission characteristics of the window depend on the material used to form the window and a thickness of the material. Thin windows or a film allow transmission of relatively low energy X-rays typically emitted from elements with relatively low atomic numbers. In other words, thicker windows may prevent transmission of X-rays emitted from elements with relatively low atomic numbers (e.g., Sodium). Therefore, thin windows are often desirable. However, thin windows are also more prone to breaking or being damaged by a foreign object or a sample of interest during a reading process if the foreign object or sample is permitted to contact the window. There are multiple expenses incurred by an operator of the X-ray device that are brought about by a broken window. The expenses include monetary costs associated with replacing the window and also productivity costs associated with the X-ray device not being usable while the repair is being made.

Accordingly, it is desirable to have a protective device that addresses the disadvantages of the known systems described above.

BRIEF DESCRIPTION OF THE INVENTION

In one aspect, a radiation assembly includes an aperture, a window covering the aperture, the window configured to permit radiation to pass through, the window is configured to prevent the passage of fluids and particles through the aperture, and a protective device covering the window, the protective device comprising a plurality of holes at least partially aligned with the aperture, the protective device configured to permit at least some radiation to pass through the holes, the protective device is configured to prevent objects larger than the holes to contact the window and is configured to withstand external forces and prevent those forces from damaging the window.

In another aspect, a method of determining an elemental composition of a material sample includes providing a radiation source assembly including a radiation source device and a complementary radiation detector assembly including a radiation detector device wherein the radiation source assembly includes a window covering the radiation source device and the radiation detector assembly includes a window covering the radiation detector device. The method also includes covering at least one of the windows with a protective device, positioning the radiation source assembly and the radiation detector assembly proximate the material sample, and preventing the material sample from contacting the at least one of the windows using the associated protective device.

In yet another aspect, a spectrometer for determining a composition of a material sample includes a first radiation assembly comprising a radiation source device configured to generate a primary beam of radiation to be directed toward the material sample, an aperture though which, a first portion of the primary beam of radiation must pass to reach the material sample, a window covering said aperture, said window configured to permit the at least a first portion of the primary beam of radiation to pass through, said window is configured to prevent the passage of fluids and particles through the aperture, and a protective device covering said window, said protective device comprising a plurality of holes at least partially aligned with the aperture, said protective device configured to permit at least a second portion of the primary beam of radiation to reach the material sample through the holes, said protective device configured to prevent objects larger than the holes to contact the window. The spectrometer also includes a second radiation assembly including a radiation detector device configured to generate a detector signal representative of a secondary beam of radiation from the material sample generated by an interaction of the second portion of the primary beam of radiation and the material sample, an aperture though which, the secondary beam of radiation must pass from the material sample to the radiation detector device, a window covering said aperture, said window configured to permit the secondary beam of radiation to pass through, said window is configured to prevent the passage of fluids and particles through the aperture, and a protective device covering said window, said protective device comprising a plurality of holes at least partially aligned with the aperture, said protective device configured to permit at least a portion of the secondary beam of radiation to reach the radiation detector device through the holes, said protective device configured to prevent objects larger than the holes to contact the window. The spectrometer also includes a processing device coupled to said radiation source device and said radiation detector device.

DETAILED DESCRIPTION OF THE INVENTION

The methods and apparatus described herein facilitate protecting an X-ray device window. X-ray device windows are typically fragile and costly to replace if damaged. One cause of damage to X-ray device windows comes from contact with a foreign object or a sample being tested. For example, the foreign object or sample being tested may be jagged and any contact with the X-ray device window could damage or destroy the window. However, it is undesirable to increase the distance from the surface of the sample to the detector in order to prevent contact between the sample and the X-ray device window. In an example of an X-ray fluorescence (XRF) analyzer, increasing the distance from the surface of the sample to the detector causes a loss of intensity of secondary radiation emitted by the sample that is proportional to the square of the distance increase. The methods and apparatus described herein protect the X-ray device window while maintaining the sample within a predefined distance of the detector.

Figure 1:
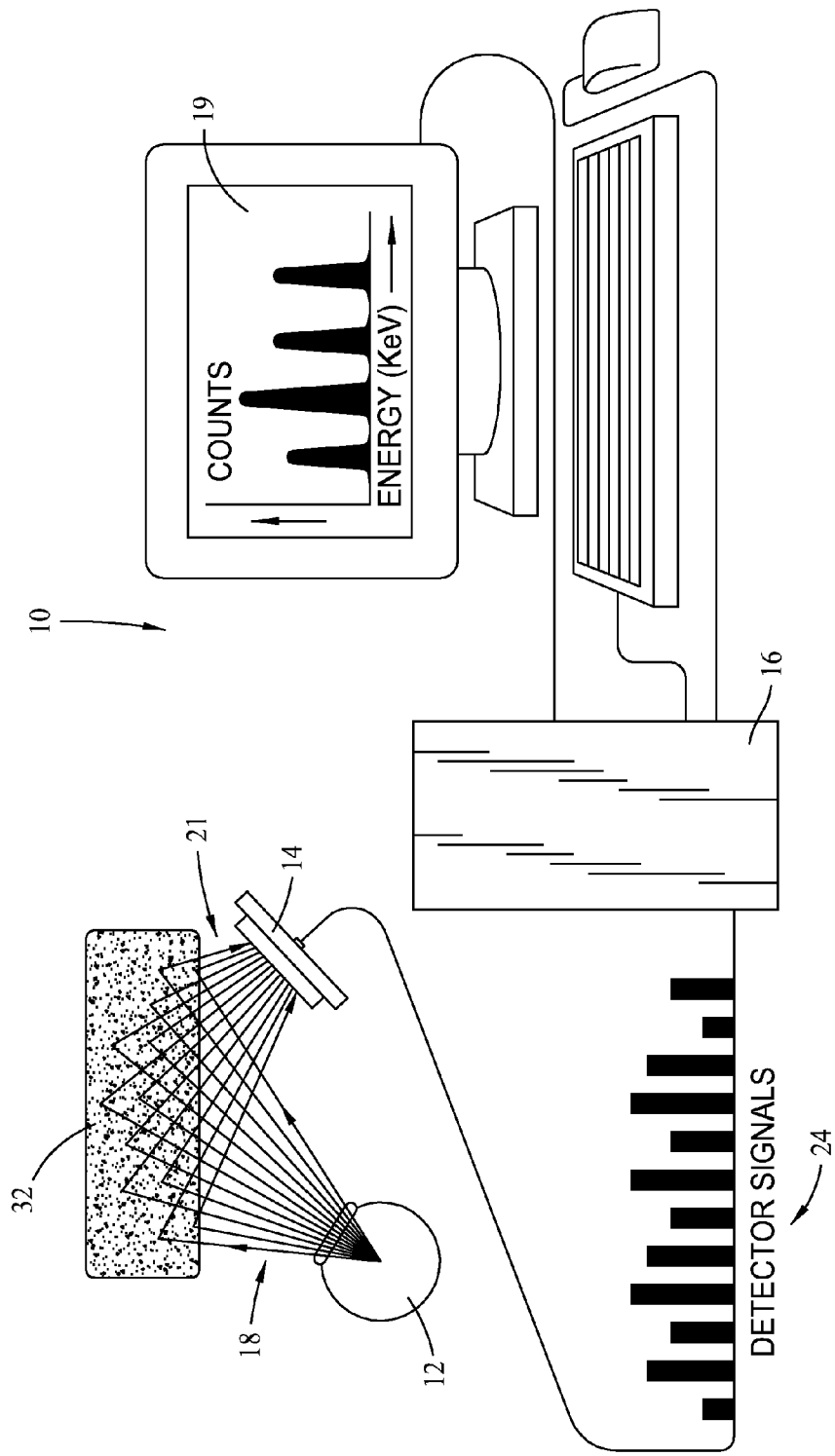
FIG. 1 is a functional illustration of the general components of a radiation assembly 10 in accordance with an exemplary embodiment of the present disclosure.

FIG. 1 is a functional illustration of the general components of a radiation assembly 10, for example, but not limited to, an X-ray fluorescence (XRF) spectrometer. XRF spectrometers detect secondary radiation emitted from a sample of material that has been excited by radiation applied to the sample material by the spectrometer. A wavelength distribution of the emitted radiation is characteristic of the elements present in the sample, while the intensity distribution gives information about the relative abundance of the elements in the sample. By means of a spectrum obtained in this manner, a user typically is able to determine the components, and quantitative proportions of those components, within the examined test sample. In the illustrated embodiment, radiation assembly 10 includes a radiation source device 12, a radiation detector device 14, an analyzer 16, and a display 19. Radiation source device 12 may include an X-ray tube that projects a primary beam 18 of X-rays towards a sample 32 that is to be tested. In another exemplary embodiment, radiation source device 12 is a radioactive isotope, which projects a primary beam of gamma rays toward sample 32. In yet another exemplary embodiment, radiation source device 12 is an electron beam source that projects a primary beam of electrons towards sample 32. Any suitable radiation source, or plurality of sources, that allow radiation assembly 10 to function as described herein may be used as radiation source device 12.

Sample 32 becomes excited after being exposed to primary beam 18 of X-rays. This excitation causes sample 32 to emit a secondary (i.e., characteristic or fluorescent) radiation 21. Secondary radiation 21 is collected by radiation detector device 14. Radiation detector device 14 includes electronic circuitry, which is sometimes referred to as a preamplifier, that converts collected secondary radiation 21 to a detector signal 24 (i.e., a voltage signal or an electronic signal) and provides the detector signal 24 to analyzer 16. In at least one embodiment, analyzer 16 includes a digital pulse processor or multi-channel analyzer.

Figure 2:
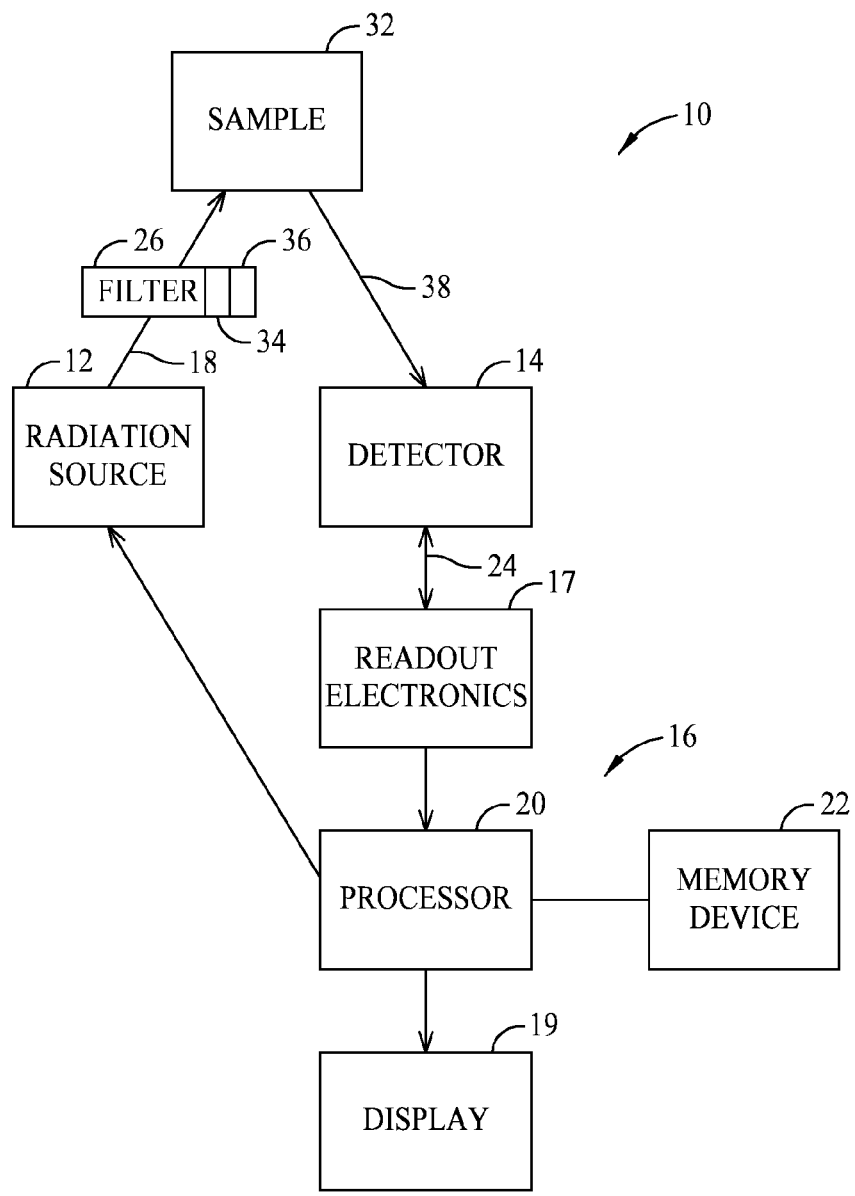
FIG. 2 is a block diagram of an exemplary radiation system in accordance with an exemplary embodiment of the present disclosure.

FIG. 2 is a block diagram of radiation assembly 10 in accordance with an exemplary embodiment of the present disclosure. In the exemplary embodiment, radiation assembly 10 includes radiation source device 12, radiation detector device 14, and analyzer 16, which in the exemplary embodiment includes a readout electronics 17, a processor 20, and a memory device 22. Radiation assembly 10 may also include a display 19 and/or a filter 26.

The terms processor or processing device, as used herein, refer to central processing units, microprocessors, microcontrollers, reduced instruction set circuits (RISC), application specific integrated circuits (ASIC), logic circuits, and any other circuit or processor capable of executing the functions described herein.

It should be noted that embodiments of the invention are not limited to any particular processor for performing the processing tasks of the invention. The terms "processor" or "processing device," as those terms are used herein, is intended to denote any machine capable of performing the calculations, or computations, necessary to perform the tasks of the invention. The terms "processor" or "processing device" also are intended to denote any machine that is capable of accepting a structured input and of processing the input in accordance with prescribed rules to produce an output. It should also be noted that the phrase "configured to" as used herein means that the processor is equipped with a combination of hardware and software for performing the tasks of embodiments of the invention, as will be understood by those skilled in the art.

Moreover, aspects of the invention transform a general-purpose computer into a special-purpose computing device when configured to execute the instructions described herein.

In the exemplary embodiment, radiation source device 12 is a radiation source that projects a primary beam of radiation toward a sample 32 that is selected to be analyzed. For example, radiation source device 12 may include an X-ray tube that projects primary beam 18 of X-rays toward sample 32. In an alternative embodiment, radiation source device 12 is a radioactive isotope, which projects a primary beam 18 of gamma rays toward sample 32. In yet another alternative embodiment, radiation source device 12 is an electron beam source that projects a primary beam 18 of electrons towards sample 32. Any suitable beam source, or plurality of sources, known in the art can be used as radiation source device 12. As used herein, sample 32 includes irregular-shaped objects, relatively small object, such as, but not limited to powders, particulates, and shavings, and objects that include protrusions and pointed extensions.

In the exemplary embodiment, filter 26 is positioned between radiation source device 12 and sample 32. For example, filter 26 may be a selectable filter coupled to processor 20. Processor 20 may be configured to select one or more of a plurality of filters that may be applied by filter 26. Processor 20 may also be configured to select that no filter be applied to primary beam 18 of X-rays. More specifically, filter 26 may include a first filter 34 that modifies characteristics of primary beam 18 of X-rays in a first manner and a second filter 36 that modifies characteristics of primary beam 18 of X-rays in a second manner. Examples of materials included within first filter 34 and/or second filter 36 include, but are not limited to, copper, aluminum, and titanium. Although described as including two filters, filter 26 may include any number of filters that allows radiation assembly 10 to function as described herein.

Sample 32 becomes excited after being exposed to primary beam 18 of X-rays. This excitation causes sample 32 to emit a secondary (i.e. characteristic fluorescent) radiation 38. Secondary radiation 38 is impinged upon radiation detector device 14. Radiation detector device 14 converts secondary radiation 38 to a detector signal 24, for example, a voltage signal or an electronic signal that is representative of secondary radiation 38. Radiation detector device 14 provides detector signal 24 to readout electronics 17, which determine an energy spectrum of the collected secondary radiation 38. Readout electronics 17 provide this energy spectrum to processor 20. Although described herein as radiation detector device 14 providing detector signal 24 to readout electronics 17 and readout electronics 17 providing the energy spectrum to processor 20, it is contemplated that readout electronics 17 and/or processor 20 may take action to receive detector signal 24 and/or the energy spectrum (e.g., may perform polling or a retrieve function in order to receive the signal and/or spectrum). Processor 20 determines the unique elemental composition of sample 32. Processor 20 may also be referred to as an analyzer and may include a digital pulse processor.

Display 19 allows an operator to view results provided to display 19 by processor 20, for example, an operator may view the energy spectrum or a derived elemental composition and a final analytical result, such as an alloy identification of sample 32. Display 19 may be built into a handheld enclosure or it may be in the form of a small handheld computer or personal digital assistant (PDA) that is communicatively coupled to processor 20.

In the exemplary embodiment, radiation assembly 10 determines measurement conditions to be applied during an analysis of a sample, for example, sample 32. As described above, processor 20 controls operation of radiation assembly 10, and more specifically, controls operation of radiation source device 12. In the exemplary embodiment, processor 20 operates radiation source device 12 in accordance with at least one predefined measurement condition to perform a first elemental analysis of sample 32. For example, processor 20 may be configured to operate radiation source device 12 in accordance with a first measurement condition or a first set of measurement conditions. The measurement condition includes, but is not limited to, a length of time the measurement is taken, a level of voltage applied to radiation source device 12, a level of current applied to radiation source device 12, and/or a type of filter 26 used. In the exemplary embodiment, a first predefined level of voltage is applied to radiation source device 12 for a first predefined length of time to perform the first elemental analysis of sample 32. The first elemental analysis may also be referred to as an initial analysis of sample 32 that provides an initial determination of an alloy grade of sample 32. The first elemental analysis is not stringent enough to determine, to a predefined level of certainty, that sample 32 is composed of the initial determination of the alloy grade. The first set of measurement conditions may be stored in a memory device, for example, memory device 22. In a specific example, an aluminum/titanium (Al/Ti) filter is positioned between radiation source device 12 and sample 32, and power having 40 kV and 10 microamps is applied to radiation source device 12 for five seconds.

Figure 3:
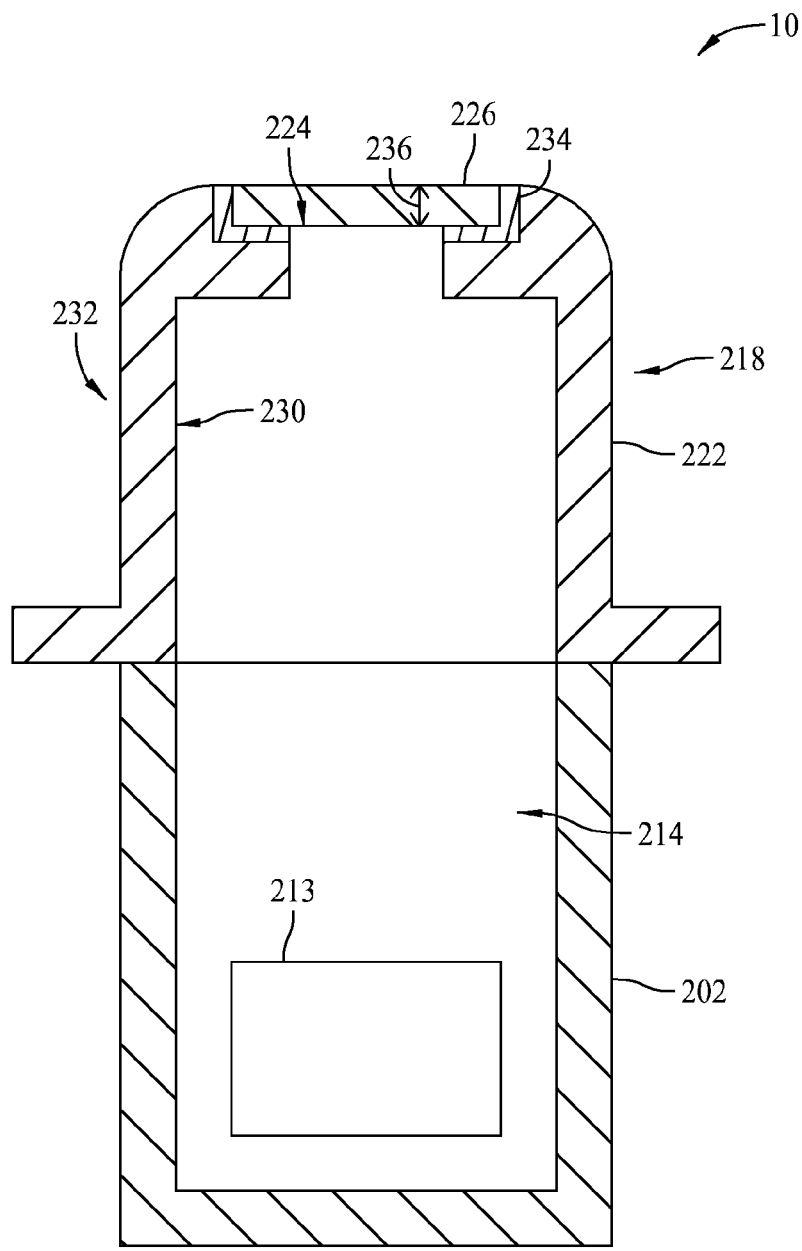
FIG. 3 is a cross-sectional view of a portion of a known radiation system.

FIG. 3 is a cross-sectional view of a portion of a known radiation assembly 10. In the illustrated embodiment, radiation assembly 10 is included within, for example, an X-ray florescence (XRF) analyzer. More specifically, radiation assembly 10 may include an X-ray assembly 213, which may include an X-ray source assembly or an X-ray detector assembly. An X-ray source assembly includes radiation source device 12 and a base 202 enclosing a chamber 214 having a controlled atmosphere. In an embodiment, chamber 214 is evacuated such that a vacuum within chamber 214. In various embodiments, chamber 214 may be filled or partially-filled with a fluid, such as an inert gas. Chamber 214 may be maintained at a vacuum or be pressurized with respect to a pressure external to chamber 214. An X-ray detector assembly includes radiation detector device 14 and chamber 214. Base 202 includes a radiation window assembly 218 through which radiation and/or electrons may pass, while the controlled atmosphere condition within chamber 214 is maintained. Although described with respect to an X-ray source assembly or an X-ray detector assembly, the methods and apparatus described herein may be applied to other types of sources/detectors, including, but not limited to, ionized radiation sources, electron emitting sources, silicon pin detectors, silicon drift detectors, and/or proportional counters. Although described herein with respect to an XRF analyzer configured to determine an elemental composition of a sample 32, radiation assembly 10 may be included within other devices.

In the illustrated embodiment, radiation window assembly 218 includes a radiation window support 222 with an opening 224 defined therein. Radiation window support 222 includes at least one wall that may form a portion of chamber 214. In the illustrated embodiment, chamber 214 is substantially cylindrically shaped, however, chamber 214 may have any shape that allows radiation assembly 10 to function as described herein. Furthermore, opening 224 is illustrated as substantially cylindrically shaped, however, opening 224 may have any suitable shape that allows radiation assembly 10 to function as described herein, for example, but not limited to, round, rectangular, a slot, and/or multiple openings having various shapes. Moreover, radiation window assembly 218 includes a window 226 coupled to radiation window support 222 and extending across opening 224. Window 226 is configured to maintain the controlled atmosphere on the inside of chamber 214 while allowing transmission of radiation and/or electrons in or out of chamber 214. Window 226 may be formed of a film or a wafer of metallic or non-metallic material, for example, window 226 may be formed from beryllium and/or any other element(s) that allow radiation window assembly 218 to function as described herein.

Radiation window support 222 includes an inner side 230 (i.e., a controlled atmosphere side) and an outer side 232 (i.e., an ambient side). Opening 224 allows for the transmission of radiation in or out of chamber 214. Window 226 is sealed against radiation window support 222, for example, using an adhesive 234. Window 226 covers opening 224 to prevent gases from entering chamber 214, thus maintaining the controlled atmosphere condition within chamber 214. Typically, a thickness 236 of window 226 is determined that allows transmission of a desired radiation while the controlled atmosphere is maintained within chamber 214. A thin window 226 is desirable for transmission capabilities, however, a thin window 226 is more susceptible to damage than a thicker window 226.

Figure 4:
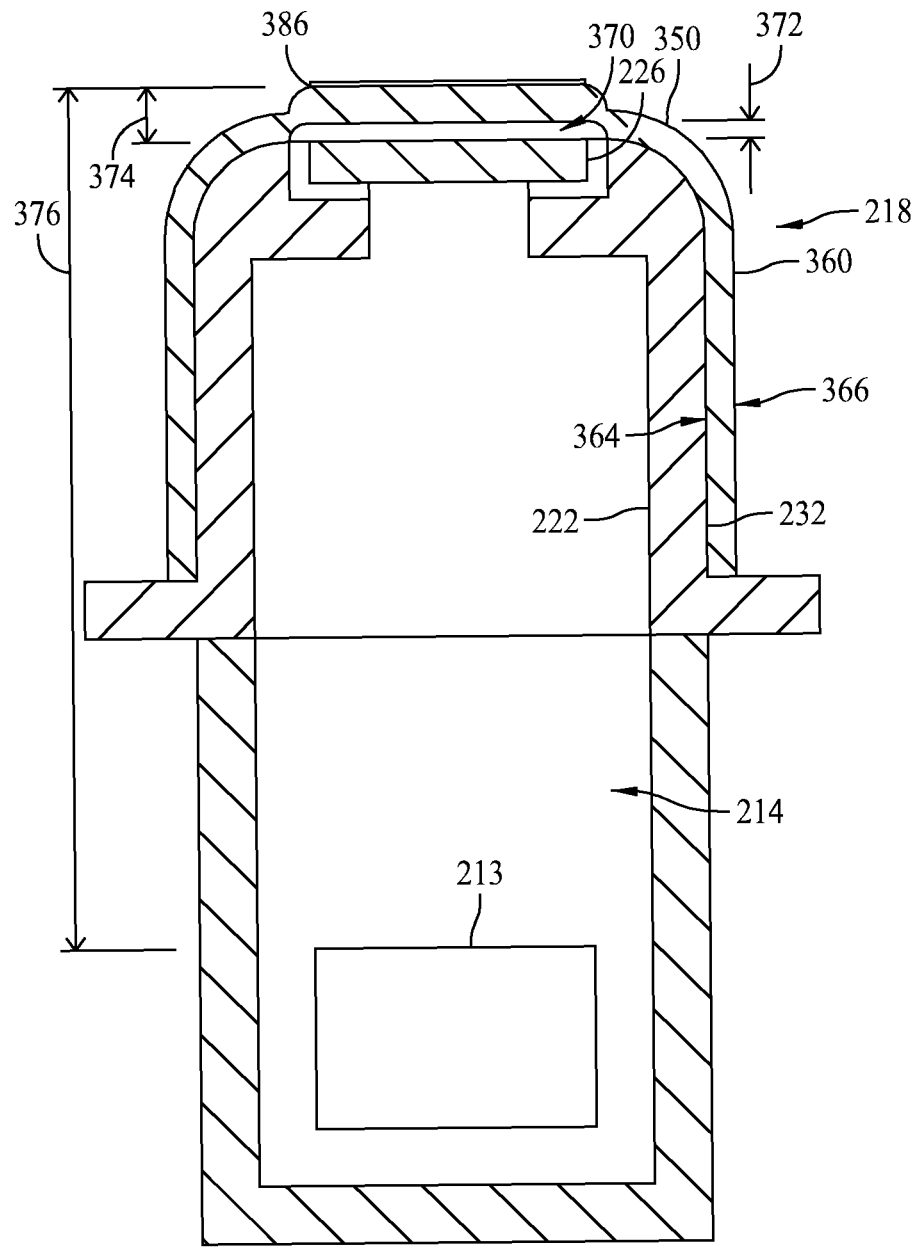
FIG. 4 is a cross-sectional view of an exemplary protective device that may be used to protect the radiation window in accordance with an exemplary embodiment of the present disclosure.
Figure 5:
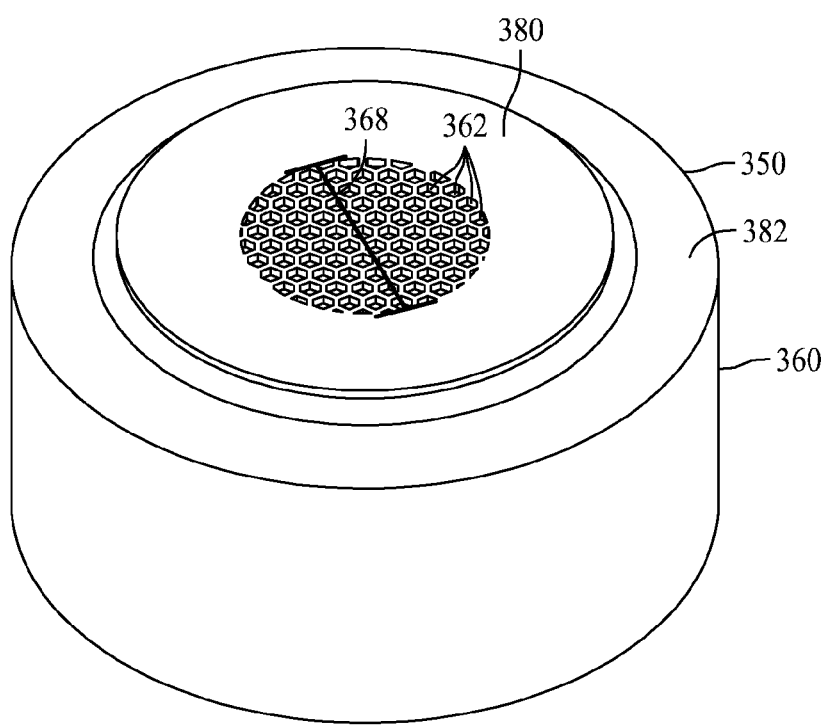
FIG. 5 is a perspective view of the protective device shown in FIG. 4.

FIG. 4 is a cross-sectional view of an exemplary protective device 350 that may be used to protect a radiation window, for example, radiation window assembly 218 (shown in FIG. 3). More specifically, protection device 350 is configured to protect window 226 included within radiation window assembly 218 (shown in FIG. 3). FIG. 5 is a perspective view of protective device 350. In the exemplary embodiment, protective device 350 includes a device support 360 that includes a first plurality of radiation path openings 362 defined therein. In the exemplary embodiment, protective device 350 is removably coupled to radiation assembly 10. For example, protective device 350 may be added to radiation assembly 10 to protect radiation window assembly 218. In an alternative embodiment, protective device 350 is included in radiation assembly 10.

In the exemplary embodiment, device support 360 includes an inner surface 364 and an outer surface 366. Device support 360 is configured to extend around at least a portion of radiation window support 222. For example, device support 360 may be configured such that, when assembled, inner surface 364 is positioned around outer side 232 of radiation window support 222. Furthermore, in the exemplary embodiment, device support 360 is configured such that protective device 350 is maintained in position around window support 222 by a press fit, an interference fit, and/or a friction fit. Alternatively, protective device 350 may be secured to radiation assembly 10 using an adhesive, a clamp, and/or any other suitable means of coupling protective device 350 to radiation assembly 10.

In the exemplary embodiment, first plurality of radiation path openings 362 are configured to allow radiation to enter and/or exit chamber 214. More specifically, first plurality of radiation openings 362 allow radiation, for example, radiation emitted from sample 32, to pass through window 226 and into chamber 214. First plurality of radiation path openings 362 also allow radiation, for example, radiation emitted by radiation source device 12, to pass from chamber 214, through window 226, and to sample 32. First plurality of radiation path openings 362 are also configured to withstand external forces and prevent those forces from damaging window 226. In the exemplary embodiment, each of first plurality of radiation path openings 362 has a substantially hexagonal shape defined within device support 360. Furthermore, in the exemplary embodiment, protective device 350 includes eighty-nine in the first plurality of radiation path openings 362 arranged in a substantially circular orientation having a first diameter 368. For example, first diameter 368 may be determined based at least partially on a size of radiation source device 12 or radiation detector device 14 included within X-ray assembly 213.

In the exemplary embodiment, a space 370 is maintained between window 226 and protective device 350. For example, protective device 350 may be maintained at a predefined distance 372 from window 226. By maintaining space 370, protective device 350 provides protection to window 226 by preventing contact between protective device 350 and window 226 and by preventing external materials (e.g., sample 32) from contacting window 226. In the exemplary embodiment, predefined distance 372 is between 0 and 1 millimeter (mm), or more specifically, between 0.25 mm and 0.75 mm, and even more specifically, approximately 0.5 mm. Furthermore, contact can be made between protective device 350 and foreign object or sample 32 without damaging window 226. This allows sample 32 to be positioned a predefined distance 374 from window 226, and therefore, a predefined distance 376 from radiation source device 12 or radiation detector device 14.

In the exemplary embodiment, device support 360 includes a first portion 380 and a second portion 382. In the exemplary embodiment, first portion 380 is manufactured from at least one metal. The material from which first portion 380 is manufactured may be any suitable material in which first plurality of radiation path openings 362 may be formed and that is structurally strong enough to protect window 226. For example, first plurality of radiation path openings 362 may be formed within first portion 380 using laser machining techniques and/or any other manufacturing technique that allows protective device 350 to function as described herein.

The material included in first portion 380 is selected to minimize interference with operation of radiation assembly 10. For example, in the example of an X-ray detector assembly, the material may be selected to minimize secondary radiation impinged upon radiation detector device 14 that emanated from first portion 380 of protective device 350. More specifically, the material may be selected to minimize an effect protective device 350 has on operation of radiation assembly 10. The material is also selected to withstand typical external forces (i.e., withstand mechanical bending potentially caused by contact between protective device 350 and a foreign object or sample 32). In some embodiments, first portion 380 of protective device 350 may be at least partially coated with a material that reduces the effect protective device 350 has on operation of radiation assembly 10. For example, first portion 380, and more specifically, edges of first portion 380 that define first plurality of radiation path openings 362, may be coated with a first coating that absorbs unwanted X-ray energies emitted by first portion 380 and which does not interfere with an analysis performed by a device in which radiation assembly 10 is included. Moreover, a second coating may be positioned over the first coating which absorbs X-ray energies emitted by the first coating and which does not produce spectral disturbances within an analytically interesting range. First and second coatings may include, but are not limited to including, indium.

In at least some embodiments, protective device 350 may include a third coating 386 covering first plurality of radiation path openings 362. Third coating 386 prevents contaminants from entering first plurality of radiation path openings 362 while allowing transmission of radiation through first plurality of radiation openings 362. Third coating 386 may include, but is not limited to including, indium, copper, silver, aluminum, and/or a polyimide film, for example, Kapton®. Kapton® is a registered trademark of DuPont™.

In the exemplary embodiment, second portion 382 is manufactured from a plastic, for example, but not limited to, polyvinyl chloride (PVC). Furthermore, in the exemplary embodiment, first portion 380 is coupled to second portion 382. For example, first portion 380 may be coupled to second portion 382 using an adhesive, a fastener, and/or any other means for coupling first portion 380 to second portion 382. Although described as including two portions, protective device 350 may alternatively be formed from a single piece of material or a number of portions exceeding two.

As described above, protective device 350 is removably coupled to radiation assembly 10. In the exemplary embodiment, protective device 350 is configured such that a press fit, interference fit, and/or a friction fit maintains second portion 382 at least partially around a portion of radiation assembly 10. In an alternative embodiment, second portion 382 is coupled to radiation assembly 10, for example, using an adhesive and/or any other suitable fastening method, and first portion 380 is removably coupled to second portion 382. In a further alternative embodiment, second portion 382 is included in radiation assembly 10 and first portion 380 is removably coupled to radiation assembly 10. By removably coupling at least one of first portion 380 and second portion 382 to radiation assembly 10, protection is provided to radiation window assembly 218 while access to radiation assembly 218 and window 226 is maintained.

Figure 6:
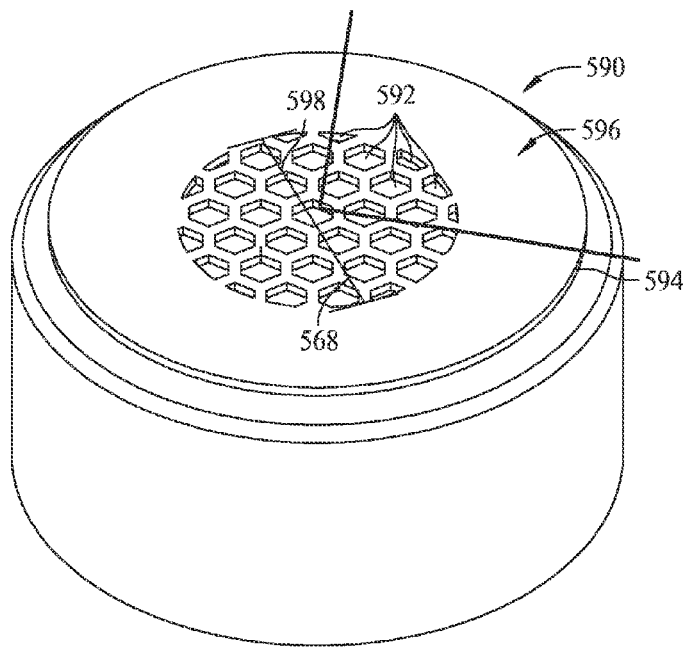
FIG. 6 is a perspective view of a first alternative embodiment of the protective device shown in FIGS. 4 and 5 a portion of which is shown in FIG. 7.
Figure 7:
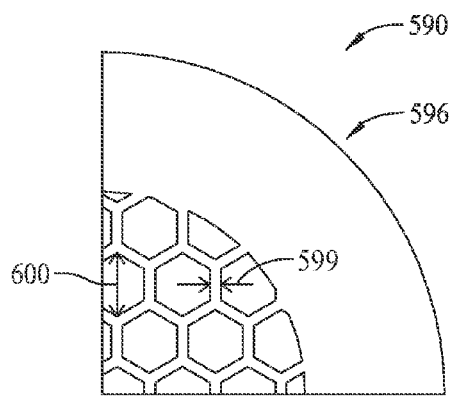
FIG. 7 is a top view of the portion shown in FIG. 6.

FIG. 6 is a perspective view of a first alternative embodiment of protective device 350 (shown in FIGS. 4 and 5) a portion 596 of which is shown in FIG. 7, and is referred to herein as protective device 590. Protective device 590 includes a second plurality of radiation path openings 592 defined within a protective device support 594. For example, in the illustrated embodiment, protective device 590 includes thirty-seven openings arranged within a circle 598 having first diameter 568. In other words, second plurality of radiation path openings 592 included within protective device 590 are larger than first plurality of radiation path openings 362 included within protective device 350.

FIG. 7 is a top view of portion 596 (shown in FIG. 6). In the exemplary embodiment, each of second plurality of radiation path openings 592 is separated from other openings by a predefined distance 599. For example, predefined distance 599 may be between 50 micrometers (μm) and 200 μm, or more specifically, between 100 μm and 150 μm, or even more specifically, approximately 146 μm. Furthermore, a diameter 600 of each of second plurality of radiation path openings 592 is predetermined such that, in combination with predefined distance 599, second plurality of radiation path openings 592 comprise a predefined percentage of circle 598 (shown in FIG. 6) having first diameter 568. For example, in the illustrated embodiment, second plurality of radiation path openings 592 may comprise between 48% and 70% of an area of circle 598, or more specifically, between 50% and 65% of an area of circle 598, or even more specifically, approximately 52% of an area of circle 598. More specifically, in a specific embodiment, to obtain an open area within protective device 590 of approximately 52%, second plurality of radiation path openings 592 are defined within device support 594 to have a diameter 600 of approximately 432 µm, spaced a distance 599 of approximately 146 µm apart, over circle 598 having first diameter 568 of approximately 2160 µm.

In the exemplary embodiment, a loss of signal caused by protective device 590 is directly proportional to the transmission of second plurality of radiation openings 592. For example, in the illustrated embodiment, 48% of radiation that would have entered chamber 214 from sample 32 will be lost due to the presence of protective device 590. The loss of signal caused by protective device 590 is also known and protective device 590 is configured such that the loss of signal is acceptable to an operator of radiation assembly 10. Without protective device 590, the operator may not position sample 32 as close to radiation detector device 14 to prevent damaging radiation window assembly 218. Increasing the distance between sample 32 and radiation detector device 14 changes the spectral content of the radiation that impinges radiation detector device 14 due to photons being absorbed by air present between sample 32 and radiation detector device 14.

Described herein are exemplary methods and apparatus for protecting window 226 of radiation window assembly 218 of radiation assembly 10. More specifically, protective device 350, 590 described herein prevents materials external to radiation window assembly 218 (e.g., foreign objects or the sample being tested) from contacting window 226 included within radiation window assembly 218. Furthermore, the protective device 350 reduces a risk of damaging window 226 if the operator of radiation assembly 10 should contact sample 32 with radiation window assembly 218. By permitting sample 32 to contact protective device 350, 590, sample 32 is maintained a predefined distance 376 from radiation source device 12 and radiation detector device 14. Moreover, protective devices 350, 590 are removably coupled to radiation window assembly 218, which allows protective device 350, 590 to be replaced if damaged, and also provides access to radiation window assembly 218 for inspection, cleaning, and/or repair.

The methods and apparatus described herein facilitate efficient and economical testing of samples using an XRF device. Exemplary embodiments of methods and apparatus are described and/or illustrated herein in detail. The methods and apparatus are not limited to the specific embodiments described herein, but rather, components of each apparatus, as well as steps of each method, may be utilized independently and separately from other components and steps described herein. Each component, and each method step, can also be used in combination with other components and/or method steps.

When introducing elements/components/etc. of the methods and apparatus described and/or illustrated herein, the articles "a", "an", "the", and "said" are intended to mean that there are one or more of the element(s)/component(s)/etc. The terms "comprising", "including", and "having" are intended to be inclusive and mean that there may be additional element(s)/component(s)/etc. other than the listed element(s)/component(s)/etc.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

The invention claimed is:

1. A radiation assembly configured to communicatively couple to a spectrum analyzer, said radiation assembly comprising:
    an enclosure having a chamber;
    an aperture extending through said enclosure;
    a window covering said aperture, said window configured to permit radiation to pass through, said window is configured to prevent the passage of fluids and particles through the aperture into said chamber;
    a protective device removably coupled to an exterior of said enclosure and covering said window, said protective device comprising:
        a plurality of holes at least partially aligned with the aperture;
        a first coating proximate said plurality of holes, said first coating configured to absorb X-rays of energies determined to interfere with a spectrum analysis performed by the spectrum analyzer;
        said protective device configured to permit at least some radiation to pass through the plurality of holes, said protective device configured to prevent objects larger than each of the plurality of holes to contact the window.

2. The radiation assembly of claim 1, further comprising a radiation source device positioned on one side of the window.

3. The radiation assembly of claim 1, further comprising a radiation detector device and a radiation source device positioned on a same side of the window.

4. The radiation assembly of claim 3, wherein said protective device is configured to contact a sample of interest to establish a predetermined optimal distance between the sample and at least one of the radiation source device and the radiation detector device.

5. The radiation assembly of claim 1, wherein said protective device comprises a second coating at least partially covering said first coating, said second coating configured to absorb X-rays emitted by said first coating.

6. The radiation assembly of claim 1, wherein said protective device comprises a third coating at least partially covering the holes.

7. The radiation assembly of claim 6, wherein said third coating is configured to prevent the passage of fluids and particles through the holes.

8. The radiation assembly of claim 1, further comprising a radiation detector device, a radiation source device, and a hollow base surrounding the radiation detector device and the radiation source device, said hollow base and said window forming an enclosed volume, said enclosed volume including a controlled atmosphere.

9. A method of determining an elemental composition of a material sample, said method comprising:
    providing a first radiation assembly including a radiation source device and a complementary second radiation assembly including a radiation detector device, the radiation detector assemblies each including a respective window covering the radiation source device or the radiation detector device;

covering at least one of the windows with a protective device;

positioning at least one of the radiation detector assemblies with the protective device proximate the material sample; and preventing the material sample from contacting the window using the protective device.

10. A method in accordance with claim 9, wherein positioning at least one of the radiation detector assemblies comprises positioning the protective device in contact with the material sample.

11. A method in accordance with claim 9, further comprising illuminating the material sample using the radiation source device, the illuminating causing fluorescence of the material sample.

12. A method in accordance with claim 11, further comprising determining, using a spectrum analyzer, components of the material sample and quantitative proportions of those components using a wavelength distribution and relative intensity of emitted fluorescent radiation.

13. A method in accordance with claim 11, further comprising determining, using a spectrum analyzer, the elemental composition of the material sample based on an emitted fluorescent radiation spectrum from the material sample, the placement of the protective device, and an amount of open area of the protective device.

14. A method in accordance with claim 9, further comprising at least one of reflecting and absorbing at least some of the radiation emitted by the radiation source device by the protective device.

15. A spectrometer for determining a composition of a material sample, said spectrometer comprising:

a first radiation assembly comprising:

a radiation source device configured to generate a primary beam of radiation to be directed toward the material sample;

an aperture though which, a first portion of the primary beam of radiation must pass to reach the material sample;

a window covering said aperture, said window configured to permit the at least a first portion of the primary beam of radiation to pass through, said window is configured to prevent the passage of fluids and particles through the aperture;

a protective device covering said window, said protective device comprising a plurality of holes at least partially aligned with the aperture, said protective device configured to permit at least a second portion of the primary beam of radiation to reach the material sample through the plurality of holes, said protective device configured to prevent objects larger than the plurality of holes to contact the window; and a second radiation assembly comprising:

a radiation detector device configured to generate a detector signal representative of a secondary beam of radiation from the material sample generated by an interaction of the second portion of the primary beam of radiation and the material sample;

an aperture though which, the secondary beam of radiation must pass from the material sample to the radiation detector device;

a window covering said aperture, said window configured to permit the secondary beam of radiation to pass through, said window is configured to prevent the passage of fluids and particles through the aperture;

a protective device covering said window, said protective device comprising a plurality of holes at least partially aligned with the aperture, said protective device configured to permit at least a portion of the secondary beam of radiation to reach the radiation detector device through the plurality of holes, said protective device configured to prevent objects larger than the plurality of holes to contact the window;

a processing device coupled to said radiation source device and said radiation detector device.

16. A system in accordance with claim 15, wherein at least one of said protective devices comprises a first coating covering at least a portion of the protective device proximate the plurality of holes.

17. A system in accordance with claim 15, wherein at least one of said protective devices comprises a first coating covering at least a portion of the protective device proximate the plurality of holes, said first coating configured to absorb X-rays of energies determined to interfere with an analysis performed by the processing device.

18. A system in accordance with claim 17, wherein at least one of said protective devices comprises a second coating at least partially covering said first coating, said second coating configured to absorb X-rays emitted by said first coating.

19. The radiation detector assembly of claim 15, wherein at least one of said protective devices comprises a third coating at least partially covering the holes, said third coating is configured to prevent the passage of fluids and particles through the holes.

* * * * *